United States Patent [19]  [11] 4,357,474
Carney et al.  [45] Nov. 2, 1982

[54] INSECT PHEROMONE

[75] Inventors: Robert L. Carney, Palo Alto; Alfred S. T. Lui, San Francisco, both of Calif.

[73] Assignee: Zoecon Corporation, Palo Alto, Calif.

[21] Appl. No.: 242,081

[22] Filed: Mar. 9, 1981

[51] Int. Cl.$^3$ .............................................. C07F 7/18
[52] U.S. Cl. ..................................... 556/482; 568/840
[58] Field of Search ......................................... 556/482

[56] References Cited

U.S. PATENT DOCUMENTS

| 3,985,813 | 10/1976 | Labovitz et al. | 556/482 X |
| 4,163,021 | 7/1979 | Cohen et al. | 556/482 X |
| 4,198,533 | 4/1980 | Carney et al. | 556/482 X |
| 4,228,093 | 10/1980 | Carney et al. | 556/482 |

Primary Examiner—Paul F. Shaver
Attorney, Agent, or Firm—Jacqueline S. Larson; Donald W. Erickson; Thomas T. Gordon

[57] ABSTRACT

Synthesis of the insect pheromone (9Z,11E)-9,11-hexadecadienal of the sugarcane borer, *Diatraea saccharalis* (F.), and intermediates therefor.

2 Claims, No Drawings

INSECT PHEROMONE

This invention relates to the synthesis of a pheromone of the sugarcane borer, *Diatraea saccharalis*, (F.), and intermediates therefor.

The compound (9Z,11E)-9,11-hexadecadienal has been reported (by A. M. Hammond et al., ESA Meeting, Atlanta, Ga., 1980) to be the sex pheromone of the sugarcane borer, which is a serious economic pest of sugarcane.

The present invention provides means for the synthesis of (9Z,11E)-9,11-hexadecadienal and intermediates therefor.

The synthesis of the present invention can be outlined as follows:

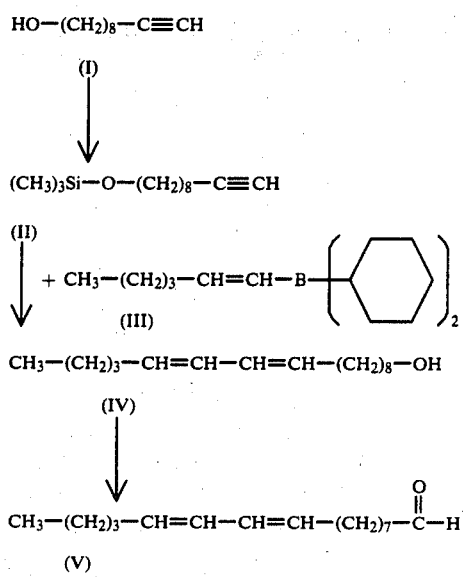

In the practice of the above-outlined synthesis, 9-decyn-1-ol (I) is converted to its trimethylsilyl ether (II) using chlorotrimethylsilane and triethylamine. The ether (II) is treated with n-butyllithium in a solvent such as tetrahydrofuran and is then reacted with (E)-1-hexen-1-yl-dicyclohexylborane (III) and tri-n-butyltin chloride in tetrahydrofuran, following the method of Zweifel et al., J. Organometal. Chem. 156:159 (1978), followed by acetic acid to yield (9Z,11E)-9,11-hexadecadien-1-ol (IV). The alcohol (IV) is oxidized to the desired aldehyde, (9Z,11E)-9,11-hexadecadienal (V), using N-chlorosuccinimide and dimethylsulfide.

The (E)-1-hexen-1-yl dicyclohexylborane (IV) can be prepared by reaction of 1-hexyne and dicyclohexylborane in a solvent such as tetrahydrofuran.

The pheromone prepared by the present invention can be used as an attractant in conjunction with insect traps as part of an integrated pest management program for detection of the sugarcane borer and determination of the need to apply pesticides. The pheromone is active at very low levels of the order of 100 to 1,000 micrograms per trap. The pheromone can be used by charging a small polyethylene cap or rubber septa which is then placed in a sticky trap.

The following examples are provided to illustrate the practice of the invention. Temperature is given in degrees Centigrade.

EXAMPLE 1

To a cooled (5°) mixture of 72 g (467.5 mmol) of 9-decyn-1-ol and 85 ml (607.8 mmol) of triethylamine in 280 ml of hexane is added dropwise, over a period of about 45 min., 71.2 ml (561.0 mmol) of chlorotrimethylsilane. After addition is complete, the mixture is stirred at room temperature for 2 hours, then is poured into ice water and extracted with hexane. The extract is washed with 2 N sulfuric acid, with water, with saturated sodium bicarbonate and with brine; is dried over magnesium sulfate; and is stripped of solvent under vacuum to give the trimethylsilyl ether of 9-decyn-1-ol.

nmr (CDCl$_3$) δ0.1 [s, 9, (CH$_3$)$_3$Si—], 1.1 →1.8 [m, 12, —(CH$_2$)$_6$—], 1.9 (t, 1, —C≡CH), 2.2 (m, 2, CH$_2$—C≡C—) and 3.5 ppm (t, 2, —CH$_2$OSi—). IR (film) 3320 cm$^{-1}$ (C≡CH) and 2120 cm$^{-1}$ (C≡C).

EXAMPLE 2

A solution of 64 g (785.0 mmol) of cyclohexene in 20 ml of tetrahydrofuran (THF) is added to 392.5 ml (392.5 mmol) of borane (1 M solution in THF) at −15°, after which the solution is stirred at 0°–5° for 1 hour to prepare dicyclohexylborane. This is cooled to −15° and 32 g (392.5 mmol) of 1-hexyne in 10 ml of THF is added dropwise. After addition is completed the reaction mixture is stirred at 0°–5° for 2.5 hours to yield a solution of (E)-1-hexen-1-yldicyclohexylborane.

A solution of 88.7 g (392.5 mmol) of the trimethylsilyl ether of 9-decyn-1-ol (from Example 1) in 100 ml of THF is cooled to −70°. To this is added, dropwise, 245.3 ml (392.5 mmol) of n-butyllithium (1.6 in hexane), after which the mixture is warmed to −40° and poured into the hexenyldicyclohexylborane solution from above. This mixture is stirred at 0° for 30 min. and then cooled to −35°. Tri-n-butyltin chloride (128 g, 124 ml) is added, and the mixture is allowed to warm to ~20° and stirred for 1.5 hours. Acetic acid (186 ml) is then added dropwise and the mixture is stirred overnight at 50°. 2 N sulfuric acid (80 ml) is then added. After 30 min., the mixture is cooled and 392.5 ml of 6 N sodium hydroxide is added, followed by the addition, in portions, of 94.2 ml of 30% hydrogen peroxide at ~30°. The reaction mixture is worked up by dilution with water and extraction with hexane. The hexane layer is washed with concentrated aqueous sodium bisulfite and with brine, dried, and stripped of solvent and cyclohexanol under vacuum (0.05 mm). The crude product is chromatographed on a column of silica gel, eluting with hexane, then 10% ether/hexane and finally 20% ether/hexane. Recrystallization from 400 ml of hexane (3X) at −60° gives (9Z, 11E)-9,11-hexadecadien-1-ol containing about 8% of the E, E isomer. This product is further purified by dissolving it in 150 ml THF, adding a solution of 3 g of tetracyanoethylene in 80 ml of THF and stirring the mixture overnight at room temperature. The THF is stripped under vacuum and the product is purified by chromatography on a column of silica gel, eluting with hexane, then 10% ether/hexane and finally 20% ether/hexane. Low temperature recrystallization (−60°) from hexane (3X 500 ml) yields the product (9Z, 11E)-9,11-hexadecadien-1-ol.

nmr (CDCl$_3$) δ2.10(m, 4, CH$_2$—C=C), 3.55 (t, 2, CH$_2$—OH) and 5.0 →6.50 ppm (m, 4, vinyl protons). IR (film) 3200 cm$^{-1}$ (—OH).

EXAMPLE 3

A mixture of 27.8 g (207.9 mmol) N-chlorosuccinimide and 450 ml of toluene is cooled to −20° to −25° and 20.4 ml of dimethylsulfide (277.3 mmol) is added all at once. The mixture is stirred at −20° for 30 min. A solution of 33 g (138.6 mmol) of (9Z, 11E)-9,11-hexadecadien-1-ol in 10 ml of toluene is added over a period of 20 min. at −15°, with occasional warming to −5°. After addition is complete, the mixture is stirred at −15° for 20 min., then warmed to −5°, and then cooled to −50° as 38.7 ml (277.3 mmol) of triethylamine is added in one portion. The suspension is allowed to warm to 0° and is then quenched with water. The phases are separated and the aqueous layer is extracted with ether (2X). The combined organic phases are washed with 2 N sulfuric acid, water, saturated sodium bicarbonate and brine and dried over sodium sulfate. Purification by chromatography on a column of silica gel, eluting with hexane, then 10% ether/hexane, followed by recrystallization from hexane at −78° yields pure (9Z,11E)-9,11-hexadecadienal.

nmr (CDCl$_3$) δ5.0 →6.50 (m, 4, vinyl protons) and 9.75 ppm (t, 1,

).

IR (film) 1720 cm$^{-1}$

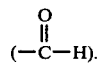).

What is claimed is:

1. The compound, the trimethylsilyl ether of 9-decyn-1-ol.
2. The compound, (9Z,11E)-9,11-hexadecadien-1-ol.

* * * * *